US009289517B2

(12) United States Patent
Goutayer et al.

(10) Patent No.: US 9,289,517 B2
(45) Date of Patent: *Mar. 22, 2016

(54) FLUORESCENT EMULSION OF INDOCYANINE GREEN

(75) Inventors: Mathieu Goutayer, Saint Malo (FR); Fabrice Navarro Y Garcia, Grenoble (FR); Isabelle Texier-Nogues, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 502 days.

This patent is subject to a terminal disclaimer.

(21) Appl. No.: 13/058,851

(22) PCT Filed: Aug. 14, 2009

(86) PCT No.: PCT/EP2009/060518
§ 371 (c)(1),
(2), (4) Date: May 2, 2011

(87) PCT Pub. No.: WO2010/018216
PCT Pub. Date: Feb. 18, 2010

(65) Prior Publication Data
US 2011/0200532 A1 Aug. 18, 2011

(30) Foreign Application Priority Data
Aug. 14, 2008 (FR) .................................... 08 55590

(51) Int. Cl.
A61K 49/00 (2006.01)

(52) U.S. Cl.
CPC ......... *A61K 49/0078* (2013.01); *A61K 49/0034* (2013.01)

(58) Field of Classification Search
None
See application file for complete search history.

(56) References Cited

U.S. PATENT DOCUMENTS

| 4,906,100 A | 3/1990 | Rice et al. |
| 5,098,606 A | 3/1992 | Nakajima et al. |
| 5,152,923 A | 10/1992 | Weder et al. |
| 5,403,575 A | 4/1995 | Kaufman et al. |
| 5,464,696 A | 11/1995 | Tournier et al. |
| 5,472,706 A | 12/1995 | Friedman et al. |
| 5,665,687 A | 9/1997 | Khayat et al. |
| 5,976,502 A | 11/1999 | Khoobehi et al. |
| 6,113,921 A | 9/2000 | Friedman et al. |
| 6,123,923 A | 9/2000 | Unger et al. |
| 6,350,431 B1 | 2/2002 | Snow et al. |
| 6,541,018 B1 | 4/2003 | Simmonet et al. |
| 6,559,183 B1 | 5/2003 | Schmid et al. |
| 6,949,257 B2 | 9/2005 | Lang et al. |
| 7,014,839 B2 * | 3/2006 | Klaveness et al. ............. 424/9.6 |
| 8,557,861 B2 | 10/2013 | Chen |
| 2002/0015721 A1 | 2/2002 | Simmonet et al. |
| 2002/0102301 A1 | 8/2002 | Schwarz |
| 2003/0152635 A1 | 8/2003 | Heurtault et al. |
| 2004/0092428 A1 * | 5/2004 | Chen et al. ......................... 514/2 |
| 2005/0079131 A1 * | 4/2005 | Lanza et al. ................. 424/1.11 |
| 2005/0129639 A1 | 6/2005 | Quemin |
| 2005/0180997 A1 | 8/2005 | Benita et al. |
| 2005/0255044 A1 | 11/2005 | Lomnes et al. |
| 2006/0222716 A1 * | 10/2006 | Schwarz et al. ............... 424/489 |
| 2006/0257493 A1 | 11/2006 | Amiji et al. |
| 2007/0053988 A1 | 3/2007 | Royere et al. |
| 2007/0092447 A1 | 4/2007 | Padilla de Jesus et al. |
| 2007/0148194 A1 | 6/2007 | Amiji et al. |
| 2010/0144899 A1 * | 6/2010 | Goutayer et al. ........... 514/772.1 |
| 2010/0284932 A1 | 11/2010 | Goutayer et al. |
| 2011/0195029 A1 | 8/2011 | Guyon et al. |
| 2011/0201695 A1 | 8/2011 | Mourier-Robert et al. |
| 2011/0274622 A1 | 11/2011 | Texier-Nogues et al. |

FOREIGN PATENT DOCUMENTS

| CN | 1676125 A | 10/2005 |
| EP | 0211258 A2 | 2/1987 |
| EP | 0406162 A | 1/1991 |
| EP | 0429248 A2 | 5/1991 |
| EP | 1010416 A | 6/2000 |
| EP | 1018363 A | 7/2000 |
| EP | 1693445 A1 | 8/2006 |
| GB | 2251381 A | 7/1992 |
| JP | 62-29511 A | 2/1987 |
| JP | 03-47527 A | 2/1991 |
| JP | 03-161430 A | 7/1991 |
| JP | 04-504108 A | 7/1992 |
| JP | 07-503976 A | 4/1995 |
| JP | 08-157325 A | 6/1996 |
| JP | 08-506081 A | 7/1996 |
| JP | 08-507515 A | 8/1996 |

(Continued)

OTHER PUBLICATIONS

Gunstone et al. 1997 Lipid Technologies and Applications. CRC Press, Edition 1: p. 672.*
Entry for "lecithin". 2005 Stedman's Medical Dictionary. Lippincott Williams & Wilkins, 28th Edition.*
Mordon et al., "Selective laser photocoagulation of blood vessels in a hamster skin flap model using a specific ICG formulation," Lasers in Surgery and Medicine 1997 US, vol. 21, No. 4, pp. 365-373 (1997).
International Search Report (ISR) in PCT/EP2009/060518 mailed Apr. 20, 2010.
Rodriguez et al., "Encapsulation and stabilization of indocyanine green within poly(styrene-alt-maleic anhydride) block-poly(styrene) micelles for near-infrared imaging", J. Biomedical Optics, vol. 13, No. 1, pp. 014025-1 to 014025-10 (Jan.-Feb. 2008); Cited in Japanese counterpart of U.S. Appl. No. 13/058,850.

(Continued)

Primary Examiner — Michael G Hartley
Assistant Examiner — Jennifer Lamberski
(74) Attorney, Agent, or Firm — Nicolas E. Seckel

(57) ABSTRACT

The present invention relates to a formulation of indocyanine green in the form of a nanoemulsion, comprising a continuous aqueous phase and at least one dispersed oily phase, in which the oily phase comprises indocyanine green, at least one amphiphilic lipid and at least one solubilizing lipid.
It relates also to a process for the preparation and to the use of the formulation.

8 Claims, 11 Drawing Sheets

(56) References Cited

FOREIGN PATENT DOCUMENTS

| | | |
|---|---|---|
| JP | 2001-519396 A | 10/2001 |
| JP | 2001-526650 A | 12/2001 |
| JP | 2006-008700 A | 1/2006 |
| JP | 2006-223306 A | 8/2006 |
| JP | 2008-514720 A | 5/2008 |
| WO | 90/06746 A1 | 6/1990 |
| WO | 9312766 A | 7/1993 |
| WO | 93/18752 A1 | 9/1993 |
| WO | 94/04197 A1 | 3/1994 |
| WO | 94/20072 A1 | 9/1994 |
| WO | 9848845 A | 11/1998 |
| WO | 98/57666 A | 12/1998 |
| WO | 99/18967 A1 | 4/1999 |
| WO | 0028971 A | 5/2000 |
| WO | 0164328 A | 9/2001 |
| WO | 2005077422 A2 | 8/2005 |
| WO | 2006/037089 A2 | 4/2006 |
| WO | 2006087156 A1 | 8/2006 |
| WO | 2006102768 A1 | 10/2006 |
| WO | 2008/102065 A | 8/2008 |
| WO | 2008125747 A2 | 10/2008 |
| WO | 2008128779 A1 | 10/2008 |

OTHER PUBLICATIONS

International Search Report (ISR) mailed Jan. 22, 2009 for International Application No. PCT/FR2008/000196 (WO2008/125747A3), corres. to U.S. Appl. No. 12/527,314.

Kalchenko et al., "Use of lipophilic near-infrared dye in whole-body optical imaging of hematopoietic cell homing", J. of Biomedical Optics, vol. 11, No. 5, Sep. 2006, p. 050507, XP002511213; Cited in ISR of co-pending U.S. Appl. No. 12/527,314.

Primo et al., "Binding and photophysical studies of biocompatible magnetic fluid in biological medium and development of magnetic nanoemulsion: a new candidate for cancer treatment", J. of Magnetism and Magnetic Materials, Elsevier, NL, vol. 310, No. 2, Mar. 2007, pp. 2838-2840, XP002447726; Cited in ISR of co-pending U.S. Appl. No. 12/527,314; Cited in ISR of co-pending U.S. Appl. No. 13/058,850.

Friedlander et al., Involvement of integrins alpha v. beta 3 and alpha v. beta 5 in ocular neovasclar diseases, 1996 Proc. Natl Acad. Sci., USA 93:9764-9769; in co-pending U.S. Appl. No. 12/527,314.

International Search Report (ISR) mailed Dec. 22, 2009 for International Application No. PCT/FR2008/050249 (WO2008/104717A3), corres. to U.S. Appl. No. 12/527,371.

Zeevi et al., "The design and characterization of a positively charged submicron emulsion contianing a sunscreen agent", Intl. J. of Pharmaceutics, Elsevier BV, NL, vol. 108, No. 1 (Jan. 1, 1994), pp. 57-68, XP008013777; Cited in ISR of co-pending U.S. Appl. No. 12/527,371.

Mason et al., "Nanoemulsions: formation, structure and physical properties", J. Phys.: Condens. Matter, vol. 18, Sep. 29, 2006, pp. R635-R665, XP002502173; Cited in ISR of co-pending U.S. Appl. No. 12/527,371.

International Search Report (ISR) mailed Dec. 22, 2009 for International Application No. PCT/FR2009/060534 (WO2010/018222A1), corres. to U.S. Appl. No. 13/058,849.

Liu et al., "A new bioimaging carrier for fluorescent quantum dots: Phospholipid nanoemulsion mimicking natural lipoprotein core", Drug Delivery: Journal of Delivery and Targeting of Therapeutic Agents, vol. 13, No. 2, pp. 159-164 (2006); Cited in ISR of co-pending U.S. Appl. No. 13/058,849.

Anonymous, 2007 AAPS Annual Meeting & Exposition—Sasol Olefins & Surfactants Product Brochure, Nov. 10-15, 2007, abstracts. aapspharmaceutica.com/ExpoAAPS07/Data/EC/Event?Exhibitors/e62/cb63fb76-28f4-4948-a6d0-ae249dae9c30.pdf (retrieved Mar. 12, 2009), cited in ISR of co-pending U.S. Appl. No. 13/058,849.

Chung et al., "Stability of the Oil-in-Water Type Triacylglyceral Emulsions," Biotechnology and Bioprocess Engineering, vol. 6, pp. 284-288 (2001), Cited in ISR of co-pending U.S. Appl. No. 13/058,849; Cited in ISR of co-pending U.S. Appl. No. 13/058,850.

Goutayer et al., "Organic Nano-Particles for Non-Invasive Fluorescence Imaging in Mice," Bulletin du Cancer (Montrouge), vol. 95, No. Sp. Iss. SI, pp. S21-S22 (2008); Cited in ISR of co-pending U.S. Appl. No. 13/058,849.

French search report (FSR) dated Mar. 12, 2009 for priority French Appl. No. 0855588 of co-pending U.S. Appl. No. 13/058,849 (w/ category codes).

Bai et al.: "A versatile bottom-up assembly approach to colloidal spheres from nanocrystals," Angewandte Chemie International Edition Wiley-Vch Verlag GmbH, Germany, vol. 46, No. 35, pp. 6650-6653 (2007); Cited in French search report of priority French Appl. No. 0855588 of co-pending U.S. Appl. No. 13/058,849.

Akkar et al.: "Formulation of intravenous Carbamazepine emulsions by SolEmuls<(>R) technology," European Journal of Pharmaceutics and Biopharmaceutics, Elsevier Science Publishers B.V., Amsterdam, The Netherlands, vol. 55, No. 3, pp. 305-312 (2003); Cited in French search report of priority French Appl. No. 0855588 of co-pending U.S. Appl. No. 13/058,849.

Anonymous: "Lipofundin MCT/LCT," B. Braun Melsungen AG Product Information, gheg.de/media/product/4623/Product_info.pdf (retrieved Mar. 12, 2009); Cited in French search report of priority French Appl. No. 0855588 of co-pending U.S. Appl. No. 13/058,849.

Liu et al., "Preparation and characterization of novel fluorescent nanocomposite particles: CdSe/ZnS core-shell quantum dots loaded solid lipid nanoparticles", J. of Biomedical Materials Research Part A, vol. 84, pp. 1018-1025 (pub. online Aug. 1, 2007); in co-pending U.S. Appl. No. 13/058,849.

Hsu et al., Behavior of soybean oil-in-water emulsion stabilized by nonionic surfactant, J. Colloid Interface Sci. 259:374-381 (2003); in co-pending U.S. Appl. No. 13/058,849; in co-pending U.S. Appl. No. 13/058,850.

International Search Report (ISR) mailed Dec. 22, 2009 for International Application No. PCT/EP2009/060539 (WO2010018223A1), corres. to co-pending U.S. Appl. No. 13/058,850.

Liversidge et al., "Influence of physicochemical interactions on the properties of suppositories," International Journal of Pharmaceutics, Elsevier, BV, NL, vol. 7, No. 3 (1991), Cited in ISR of co-pending U.S. Appl. No. 13/058,850.

Bourdon et al., "A comparative study of the cellular uptake, localization and phototoxicity of meta-tetra(hydroxyphenyl) chlorin encapsulated in surface-modified submicronic oil/water carriers in HT29 tumor cells," Journal of Photochemistry and Photobiology, vol. 55, lines 2-3 (2000); Cited in ISR of co-pending U.S. Appl. No. 13/058,850.

Bourdon et al., "Biodistribution of meta-tetra(hydroxyphenyl)chlorin incorproated into surface-modified nanocapsules in tumor-bearing mice," Photochemical and Photobiological Sciences, vol. 1, No. 9, pp. 709-714 (2002); Cited in ISR of co-pending U.S. Appl. No. 13/058,850.

Primo et al., "Photophysical studies and in vitro skin permeation/retention of Foscan/nanoemulsion (NE) applicable to photodynamic therapy skin cancer treatment," Journal of Nanoscience and Nanotechnology, vol. 8, No. 1, pp. 340-347 (2008); Cited in ISR of co-pending U.S. Appl. No. 13/058,850.

Reddi, "Role of delivery vehicles for photosensitizers in the photodynamic therapy of tumors," J. of Photochemistry and Photobiology, Biology, Elsevier Science, Basel, Switzerland, vol. 37, No. 3, pp. 189-195 (1997); Cited in ISR of co-pending U.S. Appl. No. 13/058,850.

Mehnert et al., "Solid lipid nanoparticles production, characterization and applications," Advanced Drug Delivery Reviews, Elsevier BV, Amsterdam, Netherlands, vol. 47, No. 2/03, pp. 163-196 (2001); Cited in ISR of co-pending U.S. Appl. No. 13/058,850.

Bouchemal et al., "Nano-emulsion formulation using spontaneous emulsification: solvent, oil and surfactant optimisation", Int'l J. of Pharmaceutics 280 (2004) 241-251; in co-pending U.S. Appl. No. 13/058,850.

Heurtault et al., "Physico-chemical stability of colloidal lipid particles", Biomaterials 24 (2003) 4283-4300; in co-pending U.S. Appl. No. 13/058,850.

(56) References Cited

OTHER PUBLICATIONS

International Search Report (ISR) mailed Jan. 15, 2010 for International Application No. PCT/IB2009/006766 (WO2010/018460A1), corres. to U.S. Appl. No. 13/058,984.

Teixeira et al., "Factors Influencing the Oligonucleotides Release From O-W Submicron Cationic Emulsions". Journal of Controlled Release, Elsevier, vol. 70, No. 1/02, pp. 243-255, XP 001197324, ISSN: 0168-3659 (Jan. 29, 2001); Cited in ISR of co-pending U.S. Appl. No. 13/058,984; in co-pending U.S. Appl. No. 13/058,984.

Teixeira et al., "Characterization of Oligonucleotide Lipid Interactions in Submicron Cationic Emulsions: Influence of the Cationic Lipid Structure and the Presence of PEG-Lipids", Biophysical Chemistry, vol. 92, No. 3. pp. 169-181, XP001197325, ISSN: 0301-4622, (Sep. 18, 2001); Cited in ISR of co-pending U.S. Appl. No. 13/058,984.

Chattopadhyay et al., "Chemistry and Biology of N-(7-nitrobenz-2-oxa-1,3-diazol-4-yl)-labeled lipids: Fluorescent Probes of Biological and Model Membranes", Review Article, Chemistry and Physics of Lipids, vol. 53, No. 1, pp. 1-15, XP024783533, ISSN: 0009-3084, (Mar. 1, 1990); Cited in ISR of co-pending U.S. Appl. No. 13/058,984.

Chen et al., "Fast Release of Lipophilic Agents From Circulating PEG-PDLLA Micelles Revealed by In Vivo Forster Resonance Energy Transfer Imaging", Langmuir, vol. 24, No. 10, pp. 5213-5217, XP002510881, ISSN: 0743-7463, (Aug. 2, 2008); Cited in ISR of co-pending U.S. Appl. No. 13/058,984.

Lundberg, "Preparation of drug-carrier emulsions stabilized with phosphatidylcholine-surfactant mixtures", J. Pharm. Sci., vol. 83, pp. 72-75 (1994); in co-pending U.S. Appl. No. 12/527,314.

Weyenberg et al., "Cytotoxicity of submicron emulsions and solid lipid nanoparticles for dermal application", Int'l J. Pharmaceutics, vol. 337, pp. 291-298 (2007); in co-pending U.S. Appl. No. 13/058,850.

Jiang et al., "γ-tocopherol, the major form of vitamin E in the US diet, deserves more attention", Am. J. Clin. Nutr. 2001; 74:174-22.

Gattefosse, Suppocier(R) AS2 Pellets, www.gattefosse.com/en/applications/suppocire-as2-pellets.html (retrieved Nov. 14, 2015); Cited by Examiner in co-pending U.S. Appl. No. 13/058,850 (total 1 page).

Office Action dated Nov. 18, 2015 in co-pending U.S. Appl. No. 13/058,850 (total 14 pages).

\* cited by examiner

A

B

FLUORESCENT EMULSION OF INDOCYANINE GREEN

The present invention relates to a novel formulation of indocyanine green which can be used as a diagnostic agent, in particular for fluorescence imaging, and to a process for the preparation thereof and uses thereof.

JOINT RESEARCH AGREEMENT

This application is for a claimed invention which was made on or on behalf of parties to a Joint Research Agreement (JRA). The parties to the JRA are:

Commissariat à l'Energie Atomique et aux Energies Alternatives ("CEA"),

Centre National de la Recherche Scientifique ("CNRS"),

Université Pierre et Marie Curie ("Paris 6").

PRIOR ART

Fluorescence imaging is an imaging technique which is based on the injection of a fluorescent label into an animal or human and detection of the localisation of the fluorescent label. The instrumentation accordingly comprises an excitation source for the fluorescent label and a detector for the fluorescence emitted by the label.

Nowadays, fluorescence imaging appears as a complementary imaging technique to other modalities such as MRI (magnetic resonance imaging), PET (positron emission tomography), SPECT (single photon emission computed tomography), ultrasonic echography, radiography or X-ray tomography.

Fluorescence imaging has a number of advantages over the other imaging techniques:

it does not use ionising rays and therefore does not require radiological protection or the complex management of radioactive waste;

the instrumentation is inexpensive, compact and simple to use;

the acquisition times are very short;

it is a technique that is very sensitive in terms of the concentration of label to be injected, the concentration of label is much lower than for MRI and similar to that used in PET and SPECT;

it is a technique whose resolution is similar to that of nuclear imaging (PET, SPECT) when imaging is carried out non-invasively on the scale of a small animal or an organ, and which can have cellular resolution when microscopy techniques are used.

At present, fluorescein and indocyanine green are approved fluorophores in the United States for injection in humans.

Indocyanine green, which is referred to hereinbelow as ICG, is sold under the name Cardiogreen (Akorn Inc.), Infracyanine (Serb), ICG-Pulsion (Pulsion Medical System). The compound has the following formula:

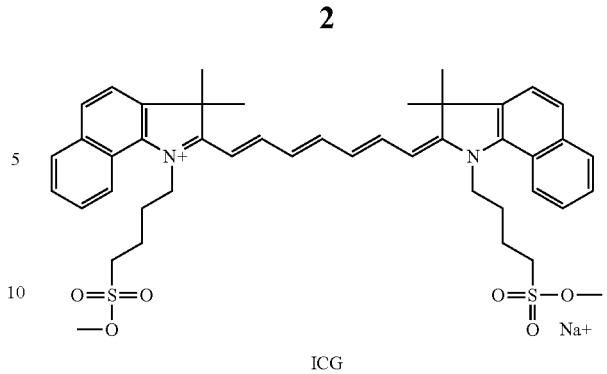

ICG

It is a fluorophore which emits in the near-infrared. That range is of particular interest for fluorescence imaging because, compared with the visible range, the tissues absorb the light less, the tissues diffuse the light less, and the autofluorescence of the tissues is reduced.

For that reason, indocyanine green is nowadays the fluorophore of choice for clinical applications of fluorescence imaging.

However, ICG has some properties which render its use as a fluorescent label problematic.

First of all, ICG is an amphiphilic compound with a solubility of from 5 to 10 mg/ml and is therefore poorly soluble in water. At higher concentrations, dimers or aggregates having different spectral properties are formed.

Moreover, ICG has poor stability and a low fluorescence quantum yield in aqueous solution, especially because of the formation of those poorly emissive dimers. Therefore, the FDA requires the solutions to be prepared less than 10 hours before injection into the patient.

In addition, ICG is adsorbed on plasma proteins to a considerable degree when injected by the intravenous route, which alters the absorption and emission spectrum.

Furthermore, the fluorescence lifetime of ICG (0.5 ns) is very close to that of the autofluorescence of biological tissues (typically 0.3-0.4 ns). It is therefore difficult to distinguish the ICG fluorescence from the tissue autofluorescence using a fluorescence device based on pulsed luminous excitation.

Finally, ICG does not have a grafting group allowing it to be coupled to targeting biomolecules or molecules such as antibodies, peptides, saccharides, proteins, oligonucleotides or aptamers. The grafting of targeting molecules is valuable because, after systemic injection, it allows the fluorophore to be directed in vivo to the zone of interest, which would result in the preferential accumulation of ICG in the zone to be imaged and consequently in an increase in the detection sensitivity.

A number of ICG formulations have been proposed for overcoming some of those problems.

Accordingly, for the treatment of lesions by photocoagulation, patent application WO 2001/017561 proposes formulations of ICG which allow its solubility and chemical stability to be increased, which formulations comprise alcohol, buffers, surfactants, glycerol, polyethylene glycol (PEG), polyvinylpyrrolidone (PVP), oils, red blood cells, fatty acids and antimicrobial agents. Patent application US 2004/0156782 describes formulations of ICG in lyophilised form for angiography, measuring hepatic or cardiac clearance, or measuring blood flow.

Patent application WO 2003/057259 describes a formulation of ICG which is based on liposomes and allows the solubility of the fluorophore to be increased. The location of the fluorophore is not specified. However, given that the fluorophore is added after formation of the liposomes, it is to be assumed that it is adsorbed at their surface. Moreover, the stability of this formulation is less than one month. Finally, liposomes are vesicles with a double-layer shell and generally have particle sizes greater than 100 nm in diameter; solutions of particles of that size diffuse light and do not permit satisfactory extravasation of the blood circulation to tumour tissues and internalisation in the cells.

It has also been proposed to adsorb ICG on cargo molecules, especially in order to increase its blood half-life. For example, WO 2005/082423 describes conjugation by non-specific adsorption of serum albumin with ICG. However, formulations based on non-covalent adsorption bonds have low chemical stability and limit the choice of biological targeting ligands which can be used. Accordingly, small targeting peptides such as cRGD, an angiogenesis marker which has been greatly studied (Haubner et al., JACS 1996, 118, 7461-7472), cannot be associated with ICG in order to produce a fluorescent label by those methods.

Patent application US 2005/0019265 proposes a fluorophore formulation in polymersomes. However, such synthetic liposomes are complicated to synthesise, require the use of synthetic polymers and do not directly yield nanoparticles suitable for permitting successful extravasation of the blood circulation to tumour tissues and internalisation in the cells, namely less than 100 nm and even less than 50 nm.

In addition, documents U.S. Pat. No. 7,014,839 and WO 98/48846 describe a formulation of ICG in the form of an emulsion of the oil-in-water type, but without indicating the method of production or the characteristics of the emulsion. However, that type of formulation leads in most cases to emulsions in which the droplet size is too large to limit the diffusion of light and ensure satisfactory colloidal stability and furtivity after injection in vivo.

TECHNICAL PROBLEM

The proposed formulations do not allow the performance of ICG as a fluorophore for fluorescence imaging to be optimised. It was therefore desired to have available an ICG formulation which can be used for fluorescence imaging and which is stable and allows its optical properties to be optimised, especially by preserving them from the external environment, and which permits access to transparent formulations which, after injection, exhibit satisfactory extravasation of the blood circulation to tumour tissues and internalisation in the cells.

SUMMARY OF THE INVENTION

According to the invention, it is proposed to formulate ICG in an emulsion comprising a solubilising lipid in the oily phase.

According to a first aspect, therefore, the invention relates to a formulation of indocyanine green in the form of a nanoemulsion, comprising a continuous aqueous phase and at least one dispersed oily phase, in which the oily phase comprises indocyanine green, at least one amphiphilic lipid and at least one solubilising lipid.

The amphiphilic lipid is preferably a phospholipid.

The solubilising lipid advantageously comprises at least one fatty acid glyceride, for example at least one glyceride of saturated fatty acids having from 12 to 18 carbon atoms.

The oily phase can further comprise at least one oil, especially an oil having a hydrophilic-lipophilic balance (HLB) of from 3 to 6, in particular soybean oil or linseed oil.

The aqueous phase preferably further comprises a cosurfactant, especially a cosurfactant having at least one chain composed of ethylene oxide units or of ethylene oxide and propylene oxide units. The cosurfactant can be chosen especially from polyethylene glycol/phosphatidylethanolamine conjugates (PEG-PE), ethers of fatty acid and polyethylene glycol, esters of fatty acid and polyethylene glycol and block copolymers of ethylene oxide and propylene oxide.

The continuous phase of the emulsion can comprise especially a physiologically acceptable buffer.

According to a second aspect, the invention relates to a process for the preparation of a formulation of indocyanine green comprising at least one continuous aqueous phase and at least one dispersed oily phase, which process comprises steps in which:
(i) the oily phase comprising at least one solubilising lipid, an amphiphilic lipid and ICG is prepared;
(ii) the oily phase is dispersed in an aqueous phase under a shearing action sufficient to form a nanoemulsion; and
(iii) the nanoemulsion so formed is recovered.

The shearing action can be exerted in particular by sonication.

The oily phase can be prepared especially by dissolving all or some of the constituents in a suitable solvent and then evaporating off the solvent.

According to a third aspect, the invention relates to the use of said formulation of indocyanine green as a diagnostic agent.

When so formulated, ICG exhibits considerably improved optical characteristics (about 10 times more performance), which allows the performance in imaging to be improved or the injected dose to be reduced. For example, 2 to 10 ml of ICG formulated as a nanoemulsion at 0.27 mg/ml emit a fluorescent signal at least as intense as 2 to 8 ml of a solution at 2.5 mg/ml ICG (dose injected intravenously in a human weighing 70 kg in order to measure the circulating blood volume and the cardiac output).

Furthermore, the formulation according to the invention is very stable, both in chemical terms and on a colloidal level and as regards the optical performance over time.

Another of the advantages of the present formulation is that it can be prepared in an isotonic medium, such as 154 mM sodium chloride, unlike ICG in suspension, which flocculates in such a medium and is therefore injected in a hypotonic medium (5% glucose water).

It is entirely suitable for use in fluorescence imaging in so far as it is preferably constituted by compounds which are today all approved for injection in humans.

The formulation of ICG according to the invention is additionally readily accessible given that it is very easy to prepare and is inexpensive.

In addition, the formulation can be adapted to different pharmaco-kinetics by modifying the molar composition of the ingredients.

Finally, the formulation according to the invention can be functionalised and therefore enables the ICG to be rendered transportable to the zone of interest that is to be imaged by means of grafting with a targeting biomolecule or molecule, which opens up new clinical applications for fluorescence imaging.

DEFINITIONS

Within the scope of the present description, the term "nanoemulsion" is understood as being a composition having at least two phases, generally an oily phase and an aqueous phase, in which the average size of the dispersed phase is less than 1 micron, preferably from 10 to 500 nm and in particular from 20 to 100 nm (see article C. Solans, P. Izquierdo, J. Nolla, N. Azemar and M. J. Garcia-Celma, Curr Opin Colloid In, 2005, 10, 102-110).

The term "droplet" includes both droplets of liquid oil as such and the solid particles obtained from emulsions of the oil-in-water type in which the oily phase is solid. In the latter case, the expression solid emulsion is also often used.

Within the scope of this description, the term "lipid" denotes the totality of the fatty materials or of the substances containing fatty acids that are present in fats of animal origin and in plant oils. They are hydrophobic or amphiphilic molecules constituted principally of carbon, hydrogen and oxygen and having a density less than that of water. Lipids can be in the solid state at ambient temperature (25° C.), as in waxes, or liquid, as in oils.

The term "phospholipid" refers to lipids having a phosphate group, especially phosphoglycerides. In most cases, phospholipids comprise a hydrophilic end formed by the optionally substituted phosphate group and two hydrophobic ends formed by fatty acid chains. Among the phospholipids, particular mention may be made of phosphatidylcholine, phosphatidylethanolamine, phosphatidylinositol, phosphatidylserine and sphingomyelin.

The term "lecithin" denotes phosphatidylcholine, that is to say a lipid formed from a choline, a phosphate, a glycerol and two fatty acids. More generally, it covers phospholipids extracted from living organisms, of plant or animal origin, in so far as they are for the most part constituted by phosphatidylcholine. Such lecithins generally constitute mixtures of lecithins carrying different fatty acids.

The expression "fatty acid" is used to denote aliphatic carboxylic acids having a carbon-containing chain of at least 4 carbon atoms. Natural fatty acids have a carbon-containing chain of from 4 to 28 carbon atoms (generally an even number). The expression long-chain fatty acid is used for a length of from 14 to 22 carbon atoms, and very long-chain fatty acid if there are more than 22 carbon atoms.

The term "surfactant" is understood as meaning compounds having an amphiphilic structure, which confers on them a particular affinity for interfaces of the oil/water and water/oil type, rendering them capable of lowering the free energy of such interfaces and stabilising dispersed systems.

The term "cosurfactant" is understood as meaning a surfactant acting in addition to a surfactant in order to lower the energy of the interface still further.

DESCRIPTION OF THE INVENTION

[Emulsion]

According to a first aspect, the invention relates to a formulation of indocyanine green in the form of a nanoemulsion, comprising at least one aqueous phase and at least one oily phase, in which the oily phase comprises indocyanine green, at least one amphiphilic lipid and at least one solubilising lipid.

The emulsion is, therefore, an emulsion of the oil-in-water type. It can be simple or multiple, especially by comprising a second aqueous phase in the dispersed phase.

The emulsion is characterised in that the oily phase comprises, in addition to the fluorophore, at least one amphiphilic lipid and at least one solubilising lipid.

The emulsion according to the invention additionally comprises in the oily phase one or more amphiphilic lipids whose purpose is to stabilise the emulsion.

Such amphiphilic lipids comprise a hydrophilic portion and a lipophilic portion. They are generally chosen from compounds in which the lipophilic portion comprises a linear or branched, saturated or unsaturated chain having from 8 to 30 carbon atoms. They can be chosen from phospholipids, cholesterols, lysolipids, sphingomyelins, tocopherols, glucolipids, stearylamines, cardiolipins of natural or synthetic origin; molecules composed of a fatty acid coupled to a hydrophilic group by an ether or ester functional group such as sorbitan esters, for example sorbitan monooleate and monolaurate sold under the names Span® by Sigma; polymerised lipids; lipids conjugated to short polyethylene oxide chains (PEG), such as the non-ionic surfactants sold under the trade names Tween® by ICI Americas Inc. and Triton® by Union Carbide Corp.; sugar esters such as saccharose mono- and di-laurate, mono- and di-palmitate, mono- and di-stearate; it being possible for said surfactants to be used on their own or in mixtures.

The amphiphilic lipid or lipids is/are preferably of natural origin and biocompatible, such as phospholipids and cholesterol.

The emulsion according to the invention additionally comprises a solubilising lipid.

The purpose of that compound is to solubilise the amphiphilic lipid, which is poorly soluble, in the oily phase of the nanoemulsion.

The solubilising lipid is chosen from compounds having an affinity for the amphiphilic lipid sufficient to permit its solubilisation. It can be an oil or a wax.

In the case where the amphiphilic lipid is a phospholipid, it can be especially a glycerol derivative, and in particular a glyceride obtained by esterification of glycerol with fatty acids.

The solubilising lipid preferably comprises at least one fatty acid glyceride. Particular preference is given to glycerides of saturated fatty acids having from 12 to 18 carbon atoms.

Advantageously, it is a mixture of different glycerides.

Preference is given to glycerides of saturated fatty acids comprising at least 10% by weight C12 fatty acids, at least 5% by weight C14 fatty acids, at least 5% by weight C16 fatty acids and at least 5% by weight C18 fatty acids.

Preference is given to glycerides of saturated fatty acids comprising from 0% to 20% by weight C8 fatty acids, from 0% to 20% by weight C10 fatty acids, from 10% to 70% by weight C12 fatty acids, from 5% to 30% by weight C14 fatty acids, from 5% to 30% by weight C16 fatty acids and from 5% to 30% by weight C18 fatty acids. The solubilising lipid is preferably solid at ambient temperature (25° C.).

Particularly preferred solubilising lipids are the mixtures of semi-synthetic glycerides sold under the trade name Suppocire®NC by Gattefossé and approved for injection in humans.

The above-mentioned solubilising lipids make it possible to obtain a formulation in nanoemulsion form which is advantageously stable. Without wishing to be bound to a particular theory, it is assumed that the above-mentioned solubilising lipids make it possible to obtain droplets in the nanoemulsion having an amorphous core. The core so obtained has a high internal viscosity without having crystallinity. Crystallisation is indeed detrimental to the stability of the nanoemulsion because it generally leads to aggregation of the droplets and/or to the expulsion of the encapsulated molecules to the outside of the droplets. These physical properties therefore promote the physical stability of the nanoemulsion and the stability of the encapsulation of indocyanine green over time.

The ICG is preferably medical-grade ICG without residual iodine.

The ICG can be used in concentrated solution in a suitable organic solvent such as ethanol, DMSO or methanol. However, solvents that are well tolerated will be preferred for in vivo application.

Preferably, the dispersed oily phase of the emulsion according to the invention additionally further comprises at least one oil.

It is preferably a biocompatible oil. Biocompatible oils are preferably used without chemical or physical modification prior to formation of the emulsion.

The biocompatible oils which can be used according to the present invention can be of natural (plant or animal) or synthetic origin. Among such oils, special mention may be made of oils of plant origin, especially soybean oil, palm oil, arachis oil, olive oil, grapeseed oil and sunflower oil; oils of animal origin, especially fish oils, synthetic oils, especially triglycerides, diglycerides, monoglycerides; it being possible for said oils to be used on their own or in mixtures. Those oils can be virgin oils, refined oils or interesterified oils.

According to a particularly preferred embodiment of the invention, the oils are chosen from the oils that are poorly soluble in water, that is to say oils that have a hydrophilic-lipophilic balance (HLB) of generally below 8 and yet more preferably from 3 to 6, such as, for example, soybean oil.

More particularly preferred is an emulsion in which the oily phase comprises at least one oil chosen from soybean oil and linseed oil.

Of course, the emulsion additionally comprises a continuous aqueous phase.

The aqueous phase preferably comprises or is constituted substantially of water or a physiologically acceptable buffer such as a phosphate buffer, for example PBS (phosphate buffered saline), or a sodium chloride solution.

However, the aqueous phase can further contain agents which allow the viscosity of the continuous phase to be increased and facilitate the emulsification, such as glycerol.

Advantageously, the emulsion according to the invention further comprises a cosurfactant.

The cosurfactant preferably has at least one chain composed of ethylene oxide units or of ethylene oxide and propylene oxide units.

Advantageously, the cosurfactant is chosen from polyethylene glycol/phosphatidylethanolamine conjugates (PEG-PE), ethers of fatty acid and polyethylene glycol, esters of fatty acid and polyethylene glycol and block copolymers of ethylene oxide and propylene oxide.

[Preparation Process]

The formulation described above is obtainable by one of the known emulsification processes, for example by sonication.

However, the formulations of the present invention are preferably obtained by a process in which the ICG is introduced into the oily phase and not into the aqueous solution.

This step provides more effective encapsulation of the fluorophore and accordingly a better fluorescence quantum yield and better stability of the resulting formulation.

Accordingly, according to a second aspect, the invention proposes a process for the preparation of the formulation of indocyanine green comprising at least one aqueous phase and at least one oily phase, which process preferably comprises steps in which:
(i) the oily phase comprising at least one solubilising lipid, an amphiphilic lipid and ICG is prepared;
(ii) the oily phase is dispersed in an aqueous phase under a shearing action sufficient to form a nanoemulsion; and
(iii) the nanoemulsion so formed is recovered.

The shearing action is preferably exerted by sonication.

In addition, it is advantageous to prepare the oily phase by dissolving all or some of the constituents in a suitable solvent and then evaporating off the solvent.

When the amphiphilic compound is soluble with difficulty, it can be of interest to prepare the oily phase by mixing the components of the dispersed phase and then dissolving the amphiphilic compound in the oil with the aid of the solubilising lipid.

The organic solvent in which the ICG is dissolved is then evaporated off.

It is then possible to add the aqueous phase prepared by mixing the components of the continuous phase.

The addition of the aqueous phase to the oily phase is preferably carried out with heating so that the oily phase is liquid.

The emulsification is carried out with strong shearing, for example ultrasonication, in order to effect the formation of a nanoemulsion.

According to a preferred embodiment of the invention, the formulation can be functionalised by the grafting of biological ligands or of molecules of interest at the surface of the nanoemulsion.

Grafting is preferably carried out on the cosurfactants, which form part of the interface between the continuous phase and the dispersed phase.

Coupling of those molecules to the cosurfactants can be carried out either before the emulsification or after the emulsification. After emulsification, it is preferred for the chemical grafting reactions to take place in aqueous solution and at a pH that is neither too acidic nor too basic (pH 5-11) so that the emulsions are not destabilised. The first variant (grafting before emulsification) is therefore preferred in principle when the chemical grafting reactions are difficult to carry out.

The molecules of interest that can be used to functionalise the emulsion according to the invention can be, for example:
a) biological ligands:
i) a biological targeting ligand: a biological entity (antibody, peptide, saccharide, aptamer, oligonucleotide, etc.) or a chemical entity (for example folic acid) which permits specific recognition of certain cells (for example tumour cells as described, for example, in the article by S. Achilefu, Technology in Cancer Research & Treatment, 2004, 3, 393-408) or of certain organs;
ii) a biological ligand which is a marker for a given biological activity, for example an enzymatic activity. For example, such biological ligands will be a peptide cleavable by a given protease, to the end of which there will be grafted an ICG fluorescence inhibitor. This type of ligand permits the specific imaging of the enzymatic activity of the protease, as is documented in the article by C. H. Tung, Biopolymers, 2004, 76, 391-403. Another example is constituted by a biological ligand having a disulfide bridge separating the label from an inhibitor of its fluorescence. That biological ligand permits the specific imaging of the internalisation of the probe in a cell, as described, for example, in French patent application FR 2 888 938;
b) a furtivity agent: this is an entity which has the effect of increasing the circulation time of ICG in the organism and of slowing down its elimination;
c) an "assembly vector": this is an entity which can permit assembly of the fluorescent label(s) and/or biological targeting ligand(s) and/or furtivity agent(s) and/or one or more functionalities (for example delivery of medicaments, other imaging modality, therapeutic function).

The emulsion can additionally contain other agents for use in the intended application, such as:

imaging agents for other imaging modalities such as MRI (magnetic resonance imaging), PET (positron emission tomography), SPECT (single photon emission computed tomography), ultrasonic echography, radiography or X-ray tomography; or molecules having a therapeutic effect (such as DNA, oligonucleotides, chemical molecules, etc.).

Such agents can be introduced into the dispersed phase or into the aqueous phase of the emulsion, or alternatively at its surface, or can be adsorbed on the dispersed phase by covalent or non-covalent bonding.

The resulting emulsion has in the dispersed phase a mean diameter of from 10 to 500 nm, more particularly from 20 to 200 nm and most particularly less than 100 nm.

Without wishing to be bound by any theory, it is currently assumed that ICG is probably both encapsulated inside the nanoemulsion and intercalated in its membrane (or shell). Given that ICG is present even before the emulsification, it appears highly unlikely that ICG is adsorbed at the surface.

The proposed formulation of ICG has excellent stability over time and additionally exhibits very good optical properties.

In addition, it permits functionalisation with a targeting ligand of interest for some applications.

[Methods of Using the Emulsion]

The proposed ICG formulation can be used particularly as a diagnostic agent.

The chemical, optical and colloidal stability, the small average diameter of the dispersed phase and the high and stable fluorescence quantum yield of ICG in the proposed formulation render it particularly valuable for fluorescence imaging.

In that application, the emulsion is to be injected into the body in order to act as a fluorescent probe, the emitted signal being collected by a suitable detection device.

An important application is the detection of sentinel nodes.

The methods which have mainly been used clinically in that field to date are scintigraphy (nuclear imaging) and dye imaging (blue dye such as patent blue, methylene blue, etc.). The labels used are in most cases conjugates of albumin in the form of nanocolloids and on which a dye has been absorbed or a radionuclide chelate, generally based on $^{99}$Tc, has been grafted. In order to avoid the use of nuclear imaging techniques, which are difficult to carry out in an operating room, fluorescence would be a technique of choice which is more sensitive and quantifiable than staining techniques.

The invention therefore relates also to a diagnostic method which comprises administering the above-mentioned formulation to a mammal. The mammal is preferably a human.

BRIEF DESCRIPTION OF THE DRAWINGS

The invention will be described in greater detail by means of the examples and the accompanying figures, which show.

EXAMPLES

Example 1

Formulation of ICG in Emulsion Form

In a suitable container there was prepared a premixture constituted by 0.05 g of soybean oil (Sigma-Aldrich), 0.150 g of semi-synthetic glycerides sold under the trade name Suppocire® NC (Gattefossé) and 0.310 mg and 9.30 mg of ICG (Cardiogreen, Sigma-Aldrich or Infracyanine Serb laboratoires) in solution in dimethylsulfoxide (DMSO) as well as 0.100 g of soybean lecithin (enriched with 45% phosphatidylcholine) sold by Lipoïd under the trade name Lipoïd® S45.

After evaporation of the DMSO in vacuo, the residue is heated to 50-60° C. and the liquid mixture is maintained at that temperature for the emulsification (at ambient temperature the mixture becomes waxy).

The continuous phase was prepared by mixing 0.05 g of glycerol, 0.331 g of polyoxyethylene stearate having 50 ethylene oxide units, sold under the trade name Myrj® 53 by ICI Americas Inc., and 154 mM sodium chloride solution to make the mixture up to 1.7 g. The solution was then kept hot (50-60° C.) before emulsification.

The aqueous solution was then added to the oil/lecithin mixture. The two-phase solution is then brought into contact with an AV505® sonicator equipped with a conical probe having a diameter of 3 mm (Sonics, Newtown) immersed approximately 1 cm in the solution. The solution was sonicated for 5 minutes with the sonicator set at 25% of the maximum power, with the following pulse sequence: 10 seconds sonication/30 seconds rest. During the sonication, the solution was maintained at 40° C. in a water bath.

The solution is then dialysed against a 154 mM sodium chloride solution with a Spectra/Por® dialysis membrane having a cutoff of 12,000 in order to remove unreacted reagents.

The resulting emulsion is filtered on a 0.22 μm filter in order to sterilise it and remove the aggregates. The emulsion can then be used directly after dilution as a fluorescent probe for functional imaging in vivo. Table 1 below summarises the composition of the formulation obtained before dialysis.

TABLE 1

Composition of the formulation of Example 1

| | | Weight mg | % by weight |
|---|---|---|---|
| Dispersed phase | Soybean oil | 50 | 2.5 |
| | Suppocire ®NC | 150 | 7.5 |
| ICG | | 0.31–9.3 | 0.015–0.465 |
| Surfactants | Lecithin | 100 | 5 |
| | Myrj 53 | 331 | 16.55 |
| Aqueous phase | Glycerol | 50 | 2.5 |
| | 154 mM NaCl solution | 1319 | 65.95 |
| Total | | 2000 | 100 |

Figure 1:
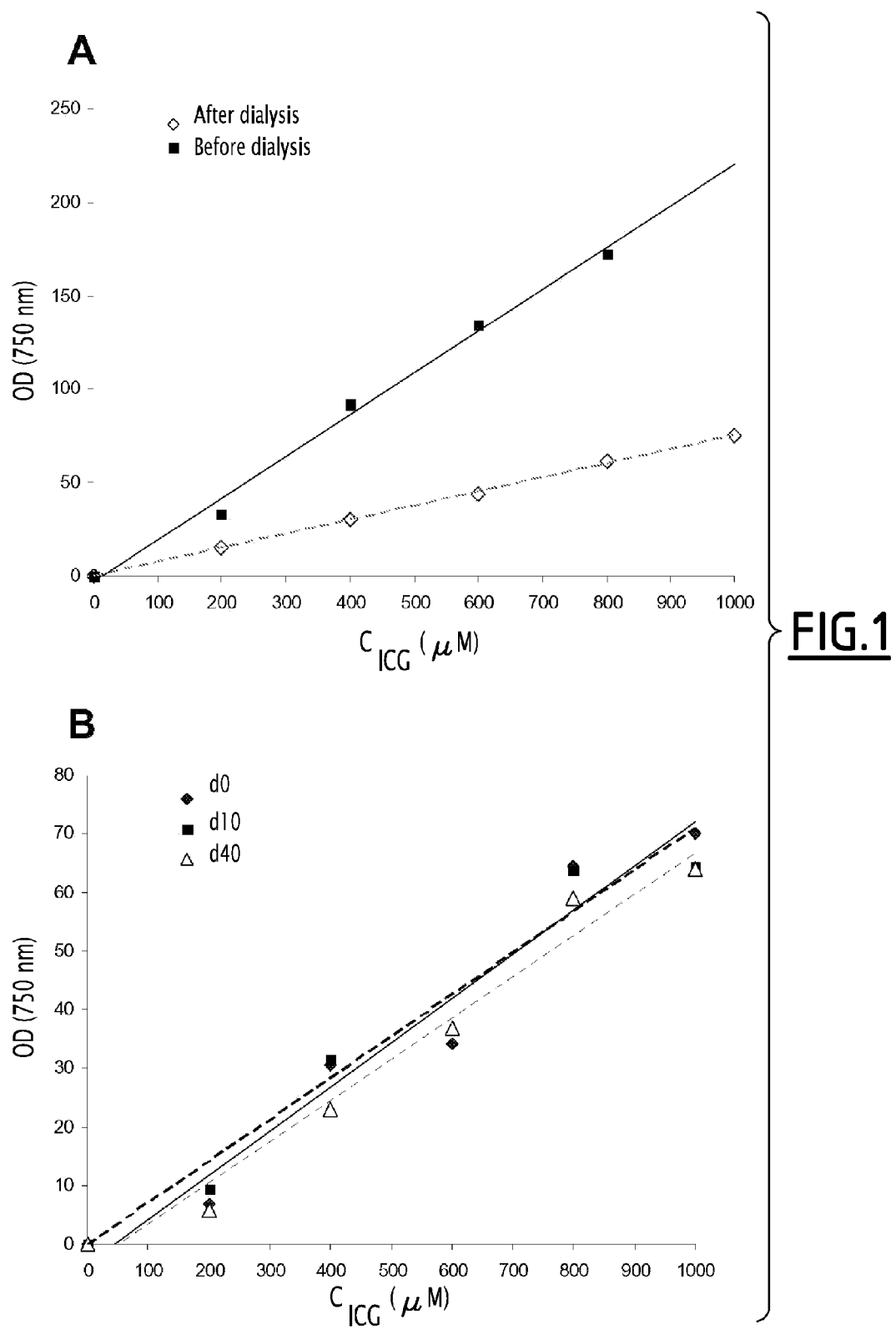
FIG. 1A: the optical density at 750 nm of ICG nanoemulsions according to Example 1 with a load rate of 0 μM to 1000 μM before and after dialysis, is determined on a CARY 300 SCAN spectrophotometer. The equation of the linear correlation line before dialysis is y=0.2235x−2.8271 with a correlation coefficient (R) of 0.997; the equation after dialysis is: y=0.0754x+0.0111 with an R of 0.999. The mean rate of incorporation of ICG into the nanoemulsions is approximately 35%.
FIG. 1B: the optical density at 750 nm of ICG nanoemulsions according to Example 1 with a load rate of 0 μM to 1000 μM dialysed 10 and 40 days after their preparation. After 10 days, the equation of the linear correlation line is: y=0.0709x−0.1805 with an R of 0.983; the equation after 40 days is: y=0.0704x−3.7455 with an R of 0.988. The rate of loss of IGC from the nanoemulsions 40 days after encapsulation is estimated at approximately 7%.

After dialysis, the excess fluorophore (not formulated in the nanoemulsions) is removed. The average rate of incorporation of ICG into the nanoemulsions is 35%, as is shown in FIG. 1A. Moreover, the ICG formulation is very stable for at least 40 days because there is no or very little loss of fluorophore 40 days after encapsulation, as is shown in FIG. 1B.

Figure 2:
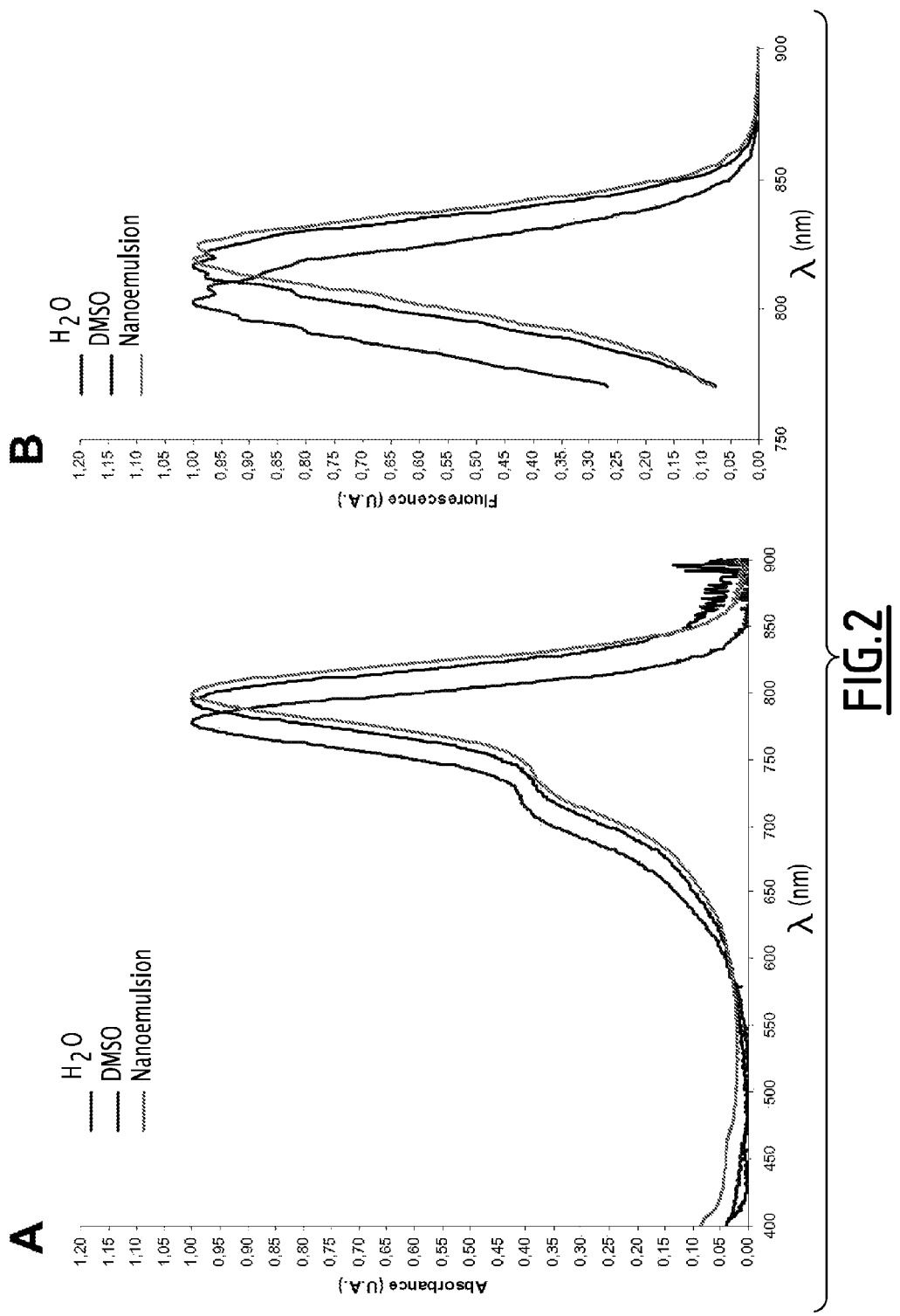
FIG. 2A: the absorption spectra of ICG in water, DMSO or formulated in the nanoemulsions according to Example 1. The ICG is dissolved in water or in DMSO at a rate of 7.75 mg/ml. The absorption spectra of ICG in water, in DMSO and encapsulated in the nanoemulsions (in a final concentration of 1 μM), determined on a CARY 300 SCAN spectrophotometer.
FIG. 2B: the fluorescence emission spectra of the same samples determined on a PERKIN ELMER LS 50B spectrofluorimeter.

The spectral characteristics of the ICG so formulated are identical to those of the ICG in DMSO, as is shown by FIGS. 2A and 2B and Table 2.

TABLE 2

Optical properties of ICG in water, in methanol, in DMSO, and as a nanoemulsion

| Fluorophore | Absorption (nm) | Emission (nm) | F | t(ps) |
|---|---|---|---|---|
| ICG in water | 777 | 802 | 0.042 | — |
| ICG in methanol | 783 | 809 | 0.16 | |
| ICG in DMSO | 793 | 817 | 0.13 | 460 ± 10 |
| ICG as a 400 µM nanoemulsion | 798 | 820 | 0.086 | 530 ± 40 |

The novel formulation obtained has a very high chemical, colloidal and optical stability (at least >40 days) as compared with that recorded in the literature (25 days in WO 2003/057259).

Figure 3:
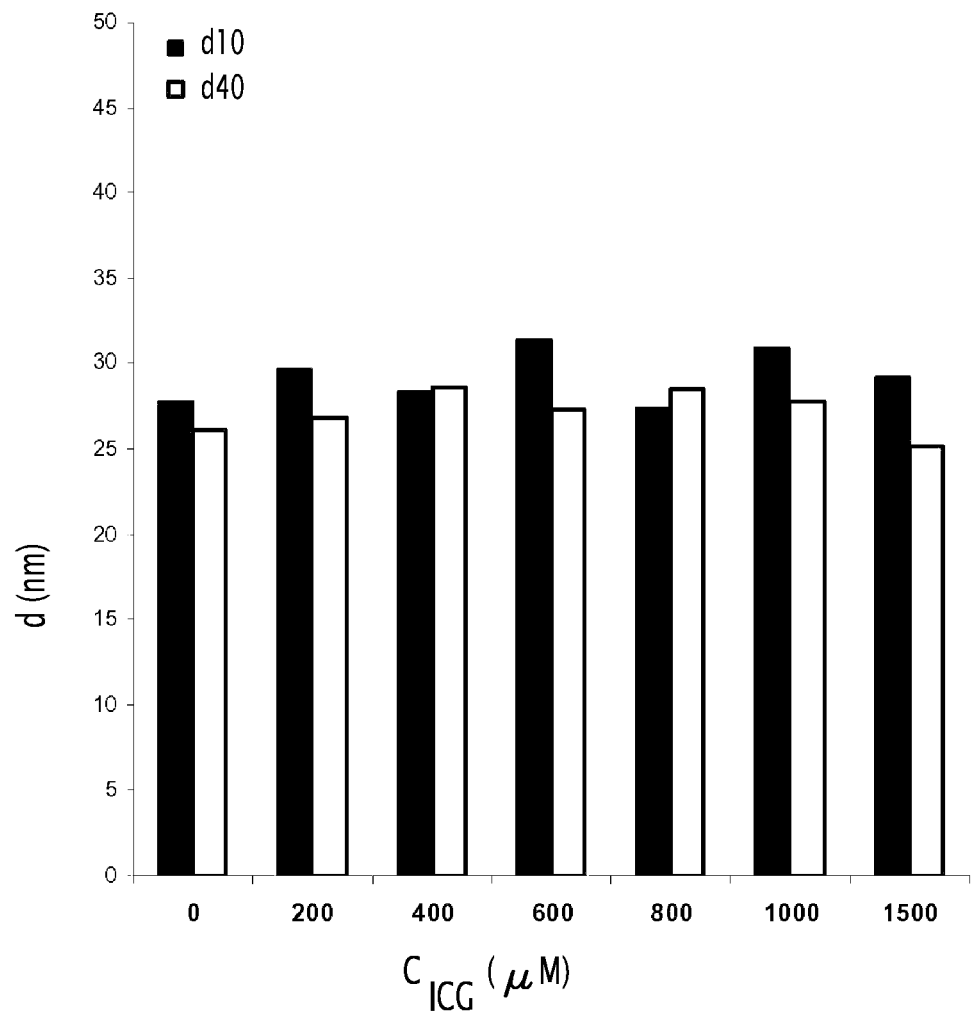
FIG. 3: a histogram of the mean diameter of the dispersed phase of the emulsions prepared as described in Example 1: 10 days (black bars) and 40 days (white bars) after dialysis. The measurements are carried out on 1 ml of a 0.1×PBS solution to which a very small volume (from 0.5 to 2 μl) of nanoemulsions containing a variable amount of ICG (load rate varying from 0 to 1500 μM) has been added, by dynamic light scattering in a ZeitaSizer Nano (Malvern Instrument)

The emulsion so obtained has a mean diameter of the dispersed phase, determined by light scattering (ZeitaSizer Nano, Malvem Instrument), of 29 nm and that diameter does not change over time, as is shown in FIG. 3.

Figure 4:
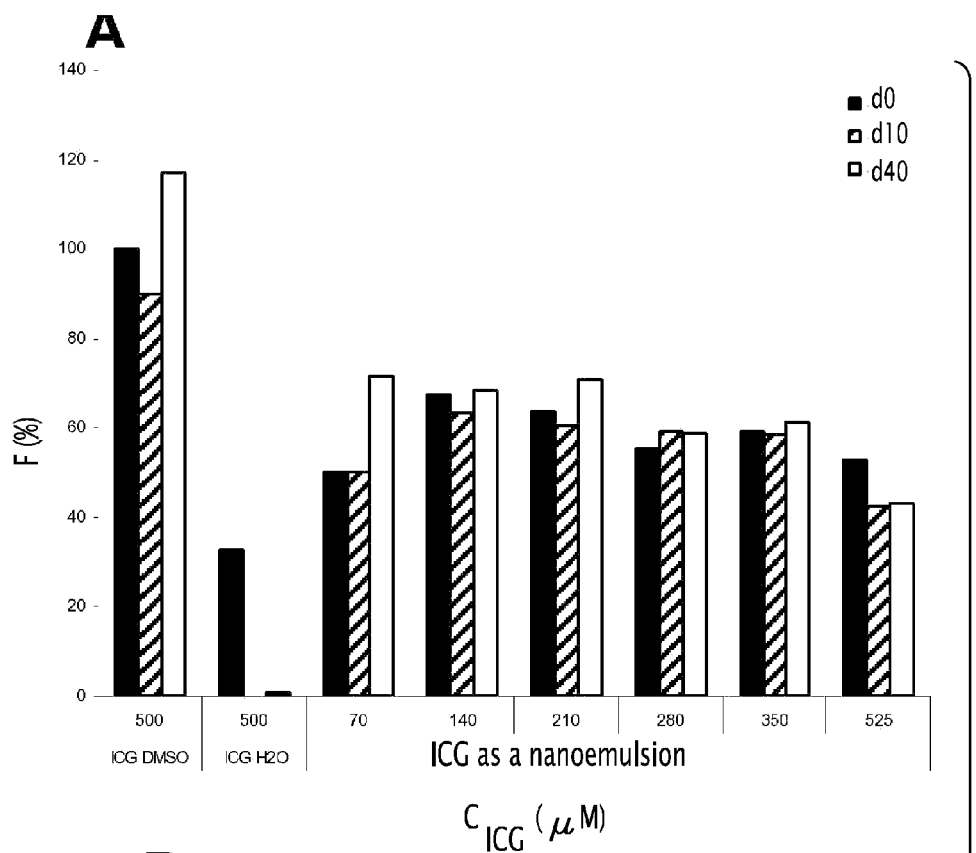
FIG. 4A: a histogram representing the fluorescence quantum yield F of ICG in solution in DMSO, in water or encapsulated in nanoemulsions according to Example 1, directly after dialysis (black bars), 10 days after dialysis (hatched bars) and 40 days after dialysis (white bars). The fluorescence quantum yield F is calculated according to the formula: $F=F_{ref} \times ((I_{fluo})/(I_{fluo})_{ref})) \times (1-10^{-Abs})_{ref}/(1-10^{-Abs})) \times (n^5_{ref}/n^2)$ where $F_{ref}$ is the fluorescence quantum yield of the reference (ICG in DMSO; $F_{ref}$=0.13), $I_{fluo}$ is the fluorescence integral of the sample, $I_{fluoref}$ is the fluorescence integral of the reference, Abs is the absorbance of the sample at the excitation wavelength, $Abs_{ref}$ is the absorbance of the reference at the excitation wavelength, $n^2_{ref}$ is the refraction coefficient of the reference (DMSO), $n^2$ is the refraction coefficient of the sample. It is to be noted that the quantum yield of ICG formulated as a nanoemulsion is stable over time, unlike that of ICG in solution in water.
FIG. 4B: a histogram representing the quantum yield F of ICG in DMSO and of different types of ICG (Cardiogreen from Sigma Aldrich or Infracyanine from Serb Laboratoires) formulated as nanoemulsions with a load rate of 1000 μM (as described in Example 1), calculated according to the formula given above. It is important to note that the improvement in the optical properties of the ICG formulated as a nanoemulsion is independent of the type of ICG used.
Figure 4:
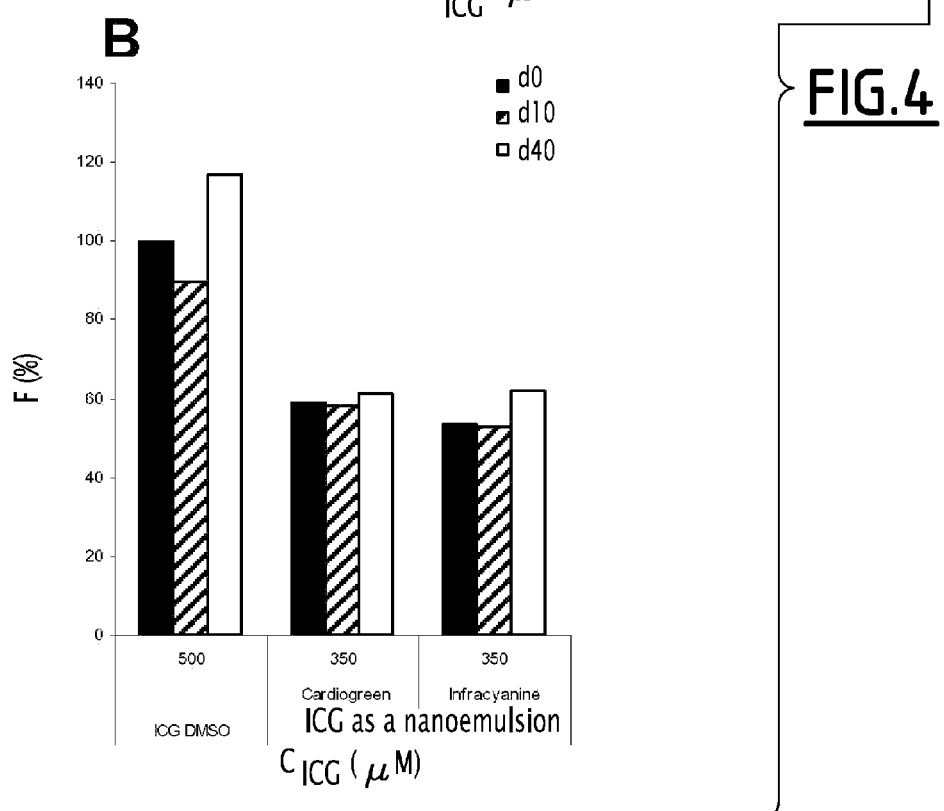

Although the fluorescence quantum yield F of ICG falls slightly when it is encapsulated as compared with that measured in DMSO, it nevertheless remains greater than that measured in water, as is shown in Table 2 and FIG. 4A. Furthermore, the quantum yield remains stable over time, unlike that of free ICG in water, as is shown in FIG. 4A, whatever the type of ICG used (Cardiogreen from Sigma Aldrich or Infracyanine from Serb laboratoires), as is shown in FIG. 4B.

Figure 5:
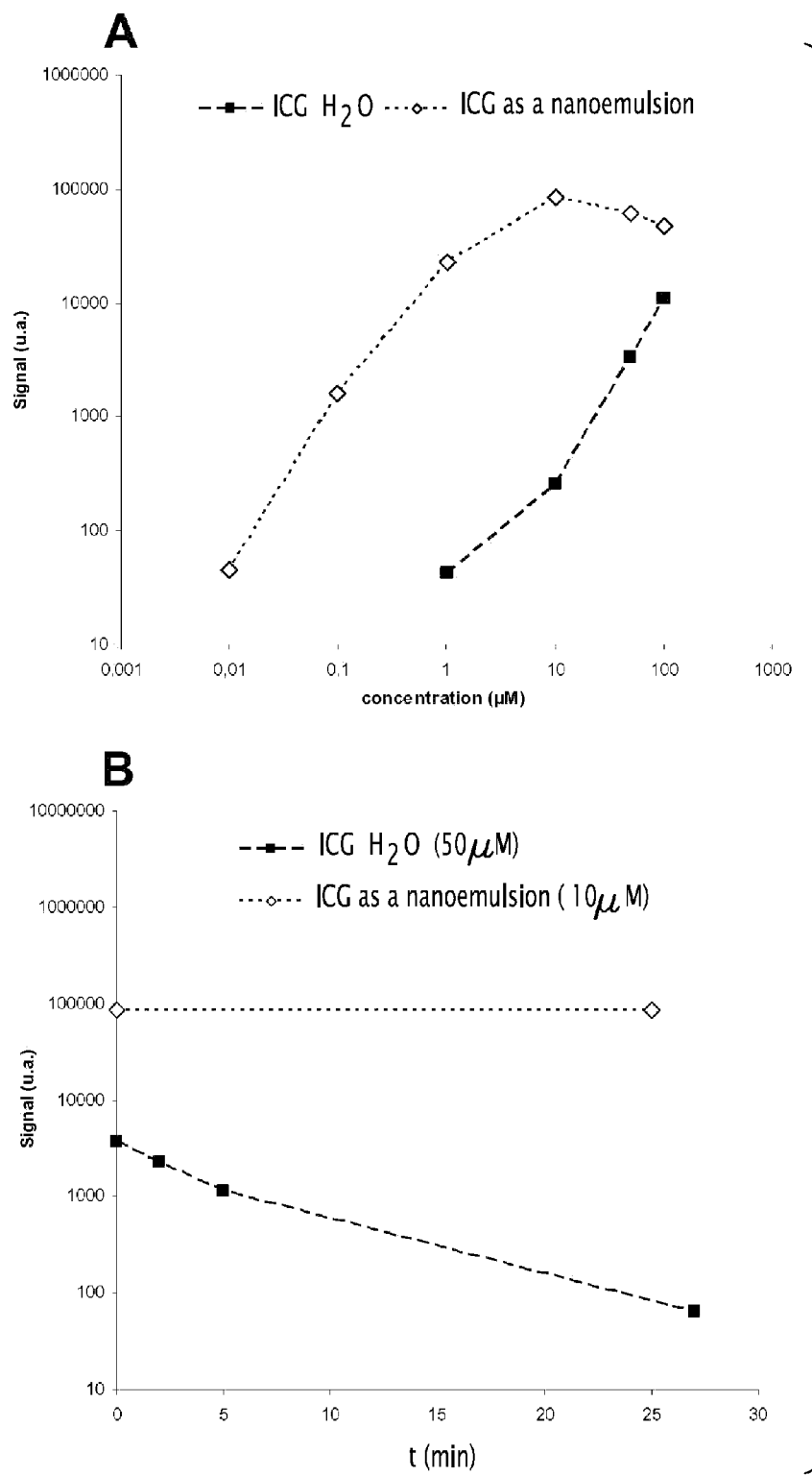
FIG. 5A: the fluorescence levels of ICG in water and of ICG encapsulated in the nanoemulsions (as described in Example 1) are shown on a logarithmic scale as a function of the concentration ranges of the two solutions, determined by an optical device composed of a light source emitting in the absorption band of ICG and a camera coupled to a suitable lens. The concentration ranges (ranging from 100 μM to 0.01 μM) of ICG in water and of ICG encapsulated in the nanoemulsions (with a load rate after dialysis of 350 μM) are prepared, respectively, in ultrapure water and in 154 mM sodium chloride, and 10 μl of each of the points of concentration are deposited in a small capillary made of PTFE and having a diameter of 1.9 mm, which is placed beneath the camera for measurement of the fluorescence level.
FIG. 5B: the fluorescence levels of the capillaries containing 2.5 nmoles of ICG in solution in water and 0.5 nmoles of ICG formulated as nanoemulsions as previously described, shown on a logarithmic scale, are measured approximately 25 minutes after the measurement shown in FIG. 5A. The reduction over time of the fluorescence level of ICG in water and the stability of that of ICG encapsulated in the nanoemulsions are to be noted.

The optimised optical properties permit a reduction in the detection threshold under a suitable measuring device, constituted by a light source emitting in the absorption band of ICG with an excitation power of the order of several mW/cm² and a camera coupled to a lens adapted to the observed sample, as indicated in FIGS. 5A and 5B.

Figure 6:
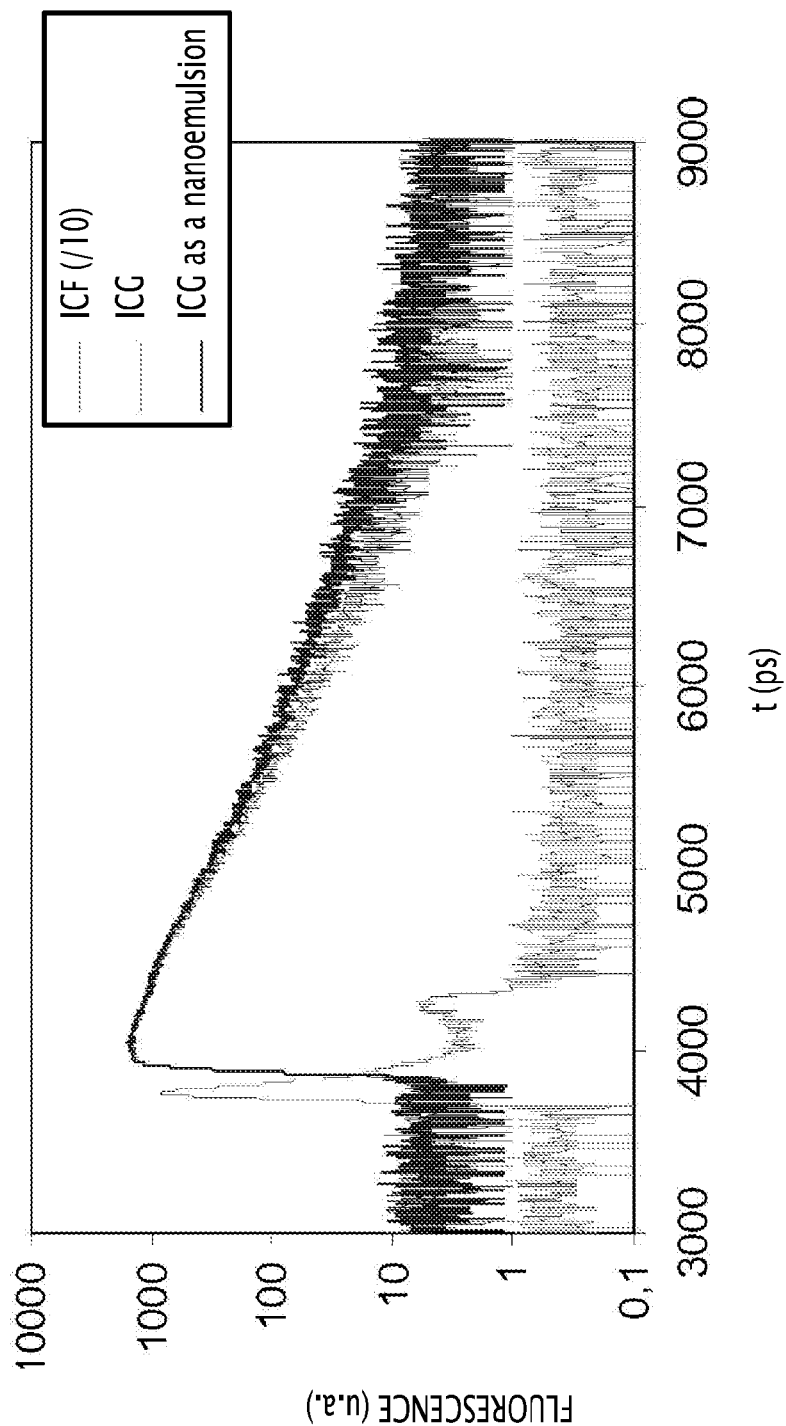
FIG. 6: the decline in fluorescence of free ICG in solution in methanol or encapsulated in the nanoemulsions in suspension in PBS (10 mM, pH 7.3), prepared according to Example 1, is measured on a measuring chain using a sapphire-titanium laser [Tsunami, Spectra-Physics, USA] (80 MHz, 100 femtoseconds), pumped by a continuous neodymium vanadate laser [Millennia Pro, Spectra-Physics, USA)] (532 nm, 5 W) and tunable in terms of wavelength from 700 nm to 100 nm. Depending on the mode of operation of the device, the laser is injected into a multimode optical fibre, used as excitatory fibre for the sample to be studied. A second optical fibre (for detection) collects the emitted fluorescence or the laser scattering via a filter system. The signal is measured by a photomultiplier tube [Hamamatsu, Japan] coupled to a TCSPC counting card [Becker & Hickel, Germany]. The latter is triggered by a portion (4%) removed from the laser signal (pulse train) via a rapid photodiode (PD) [Becker & Hickel, Germany] before being injected into the optical fibre. The measurements were made using a pulsed excitation wavelength of 740 nm. The fluorescence lifetimes t were subsequently obtained using SPCImage software (Becker Hickl GmbH) by adjustment by a monoexponential decline ($\chi_r^2$=1.0) of the deconvoluted fluorescence decline curves of the instrument response function (IRF). The results are compiled in Table 2 of Example 1.

In addition, the fluorescence lifetime t of the ICG increases when it is encapsulated, as is shown in FIG. 6 and Table 2. This property is very valuable because it allows the formulation according to the invention to be considered for use in time-resolved measuring devices.

The pictures of FIGS. 7A-7E show the value of the ICG formulation according to the invention for fluorescence imaging in particular.

In the light of all those properties, it would therefore be possible to market the formulation according to the invention in a ready-for-use form.

Example 2

Imaging of Vascularisation

Figure 7:
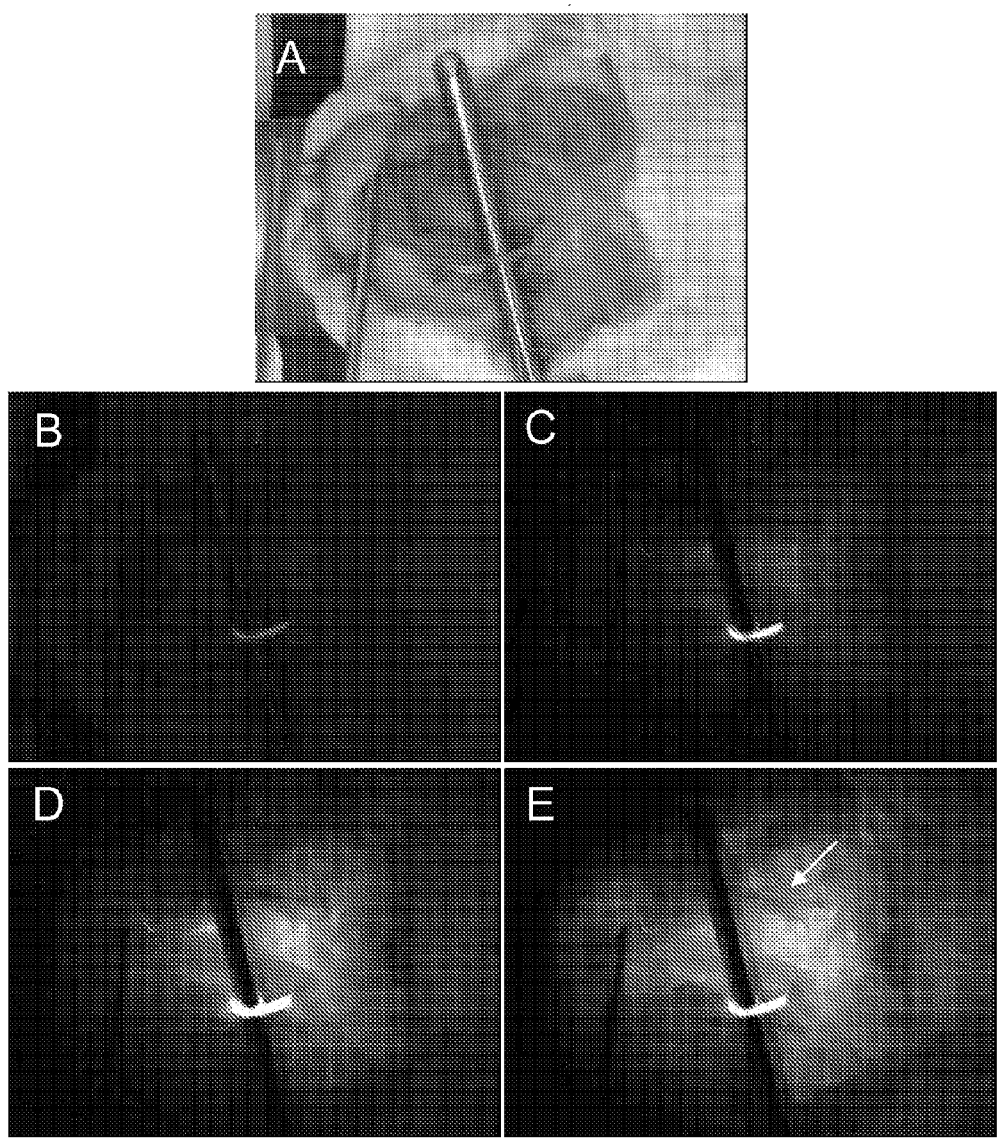
FIG. 7A-E: fluorescence imaging pictures of the vascular system in the rat as described in Example 2. The photograph shows in white light the zone imaged by the optical device. Dissection of the neck of the rat was carried out under gaseous anaesthesia (2% isoflurane) and the isolated carotid was placed above a dissection cannula. 200 μl of a solution, diluted to 225 μM, of ICG formulated as nanoemulsions (load rate after dialysis 350 μM) was then injected as a bolus into the caudal vein. Picture B shows the carotid very soon after injection (0.5 second after injection). Picture C was taken 1.5 seconds after injection and shows that the fluorescent signal becomes ever stronger as the fluorophore passes. Picture D was taken 2.5 seconds after injection and shows an even stronger fluorescent signal as the fluorophore so formulated passes. Picture E was taken 5 seconds after injection and shows that, after circulation of the ICG encapsulated in the nanoemulsions in the vascular system of the tissues of the head, an ever more intense fluorescent signal is observed in the jugular vein (white arrow). The slight fluorescent signal subsequently emitted by the surrounding tissues might correspond to the vascularisation thereof.

Male rats of the strain Sprague Dawley (Harlan France) are anaesthetised by isoflurane inhalation (4% for induction and 2% for maintenance) and then placed beneath an imaging device. The device is constituted by: 1) a light source emitting in the excitation band of ICG and the excitation power of which is of the order of several mW/cm² and 2) a CCD camera coupled to a lens adapted to the observed sample. The assembly is equipped with filters which allow the excitation light and flare to be avoided and only the fluorescence light to be collected. Dissection of the region of the neck is then carried out in order to isolate the carotid and the jugular vein. An ICG formulation prepared as described in Example 1 with a load rate of 350 µM after dialysis is then injected intravenously. Fluorescence imaging of the vascular system in that region is then carried out with visualisation firstly of the carotid and then of the jugular vein as shown in FIG. 7. This fluorescence imaging system would allow the movements of the surgeon to be guided and/or controlled during an operation.

Example 3

Imaging of Sentinel Nodes

Female mice of the strain Nude (Janvier) are anaesthetised by isoflurane inhalation (4% for induction and 2% for maintenance) and then placed beneath the fluorescence imaging device described above.

10 µl of an ICG formulation (0.5 nmole injected) prepared as described in Example 1 or of ICG dissolved in glucose water (1 nmole injected) are injected intradermally into the right rear paw.

Figure 8:
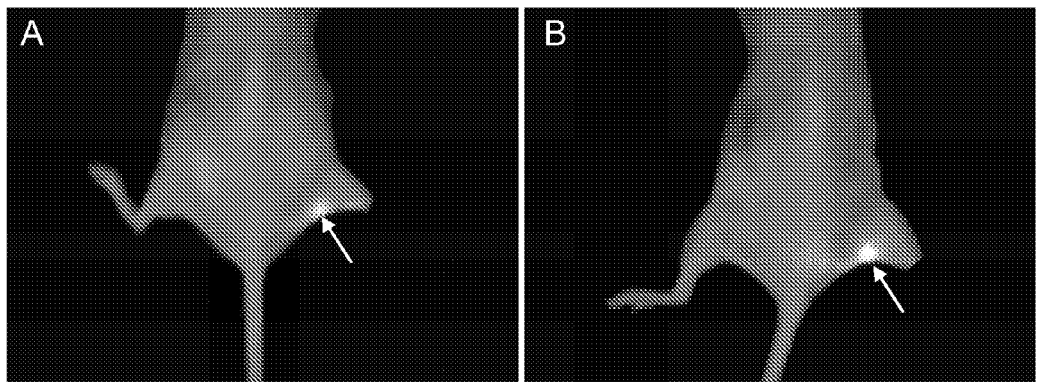
FIG. 8A-B: pictures showing a superposition between the images obtained in white light and the fluorescence images of the caudal lymph nodes (here the popliteal node represented by the white arrows) in the nude mouse after intradermal injection of ICG in solution in 5% glucose water (A) or of ICG encapsulated in nanoemulsions (B). The pictures in white light were obtained according to the same integration time (60 ms), while the fluorescence pictures were obtained according to different integration times (200 ms for picture A and 30 ms for picture B).

Temporal monitoring of the mice which had received the injections was then carried out by fluorescence imaging. It is noted that the ICG tracer formulated as nanoemulsions accumulates rapidly (from the first 5 minutes) and preferentially in the lymph nodes close to the injection site. In addition, the use of the ICG tracer formulated as nanoemulsions permits access to a more sensitive detection of the lymph nodes as compared with the results obtained using ICG formulated in 5% glucose water, as shown in FIGS. 8A and 8B.

Example 4

Tumour Imaging

Ts/Apc tumour cells of murine origin were injected subcutaneously ($10^6$ cells) into the backs of female mice of the strain Nude (Janvier), and the tumour growth in the region of the injection site is monitored for the whole of the period preceding the imaging sessions.

Two weeks later, the mice had a tumour close to the injection site and were then anaesthetised by isoflurane inhalation (4% for induction and 2% for maintenance) and then placed under the imaging device described above.

Figure 9:
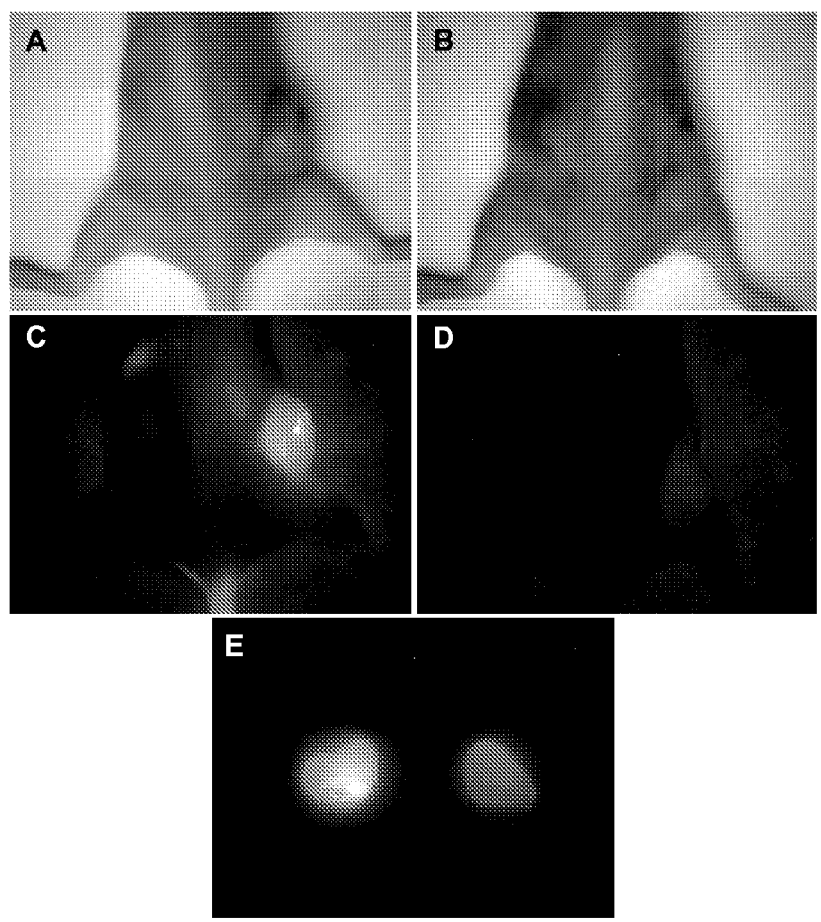
FIG. 9A-E: pictures obtained by fluorescence imaging of tumours implanted subcutaneously two weeks previously into nude mice after intravenous injection of ICG encapsulated in nanoemulsions (A, C) or of ICG in solution in 5% glucose water (B, D). Pictures A and B are obtained with the optical device without a laser in ambient light, while pictures C and D are obtained with the optical device screened from any light, under laser excitation. Picture E represents the fluorescence imaging of the tumours after excision, the tumour removed from the mouse injected with ICG formulated as nanoemulsions being on the right and the tumour removed from the mouse injected with ICG in 5% aqueous glucose solution being on the left.

A volume of 200 µl of either an ICG formulation (7 nmoles) prepared as described in Example 1 or a solution of ICG in 5% glucose water (7 nmoles) was injected intravenously into 3 of the mice in each case. One day later, a new imaging session was carried out on the anaesthetised mice (isoflurane, 2.5%) and better detection of the tumour by fluorescence imaging was observed for the ICG formulation as described in Example 1, as is illustrated in FIG. 9.

The formulation of ICG as nanoemulsions therefore constitutes a better fluorescent tracer than ICG in solution in glucose water, in particular for the visualisation of tumours.

Example 5

Emulsion with Grafted cRGD

In a suitable container equipped with stirring means, PE-PEG(5000)-maleimide is prepared by mixing 25 mg of phosphatidylethanolamine (PE, Sigma) and 100 mg of SCM-PEG 5000-maleimide (Creative Biochem) in 1 ml of methanol with 5 µl of triethylamine, and stirring is carried out at ambient temperature.

After 3 hours, the solvent and the triethylamine are evaporated off and then the resulting product, PE-PEG(5000)-maleimide, is taken up in 1 ml of methanol.

An emulsion encapsulating ICG is prepared as in Example 1 but, in addition to the 125 mg of soybean oil, 375 mg of Suppocire, 350 mg of lecithin and 1.5 mg of fluorophore as above, 25 mg of PE-PEG(5000)-maleimide previously prepared are added to the dispersed phase.

The cyclic peptide targeting αVβ3 integrins overexpressed at the surface of endothelial cells, c(RGDf[ε-S-acetylthioacetyl])K sold by Ansynth Service BV (Netherlands) and referred to as cRGD hereinbelow, has a thiol group protected in the form of a mercaptoacetic acid. 2 mg of peptide diluted in water (500 µl) are deprotected by addition of 4 µl of 0.5 M TCEP (Sigma) 30 minutes before coupling with the nanoemulsion.

For functionalisation, the emulsion is diluted in a HEPES/EDTA buffer, pH 7.4, and then the solution of cRGD peptide is added. The reaction mixture is mixed at room temperature for 1 hour. 4 µmol of 2-mercaptoethanol are added at the end of the reaction in order to quench any maleimide groups that have not reacted with the peptide.

The solution is then dialysed against PBS with a Spectra/Por® dialysis membrane having a cutoff of 12,000 in order to remove the unreacted reagents. The emulsion previously obtained is filtered on a 0.22 µm filter in order to remove the aggregates and also to sterilise it. The emulsion can then be used directly after dilution as a fluorescent probe for functional imaging in vivo.

Example 6

Demonstration of the Stability of the Nanoemulsion

The experiments below were carried out in order to demonstrate the stability conferred on the nanoemulsions by the solubilising lipid.

Example 6a

Demonstration of the High Internal Viscosity of the Droplets by NMR

A nanoemulsion comprising 255 mg of Suppocire® NC (Gattefossé) (solubilising lipid), 85 mg of soybean oil (Sigma Aldrich) (oil), 345 mg of Myrj52® (ICI Americas Inc.) (cosurfactant), 65 mg of Lipoid® s75 (lecithin, amphiphilic lipid) and a phosphate buffer (PBS) was prepared following the protocol of Example 1.

Figure 10:
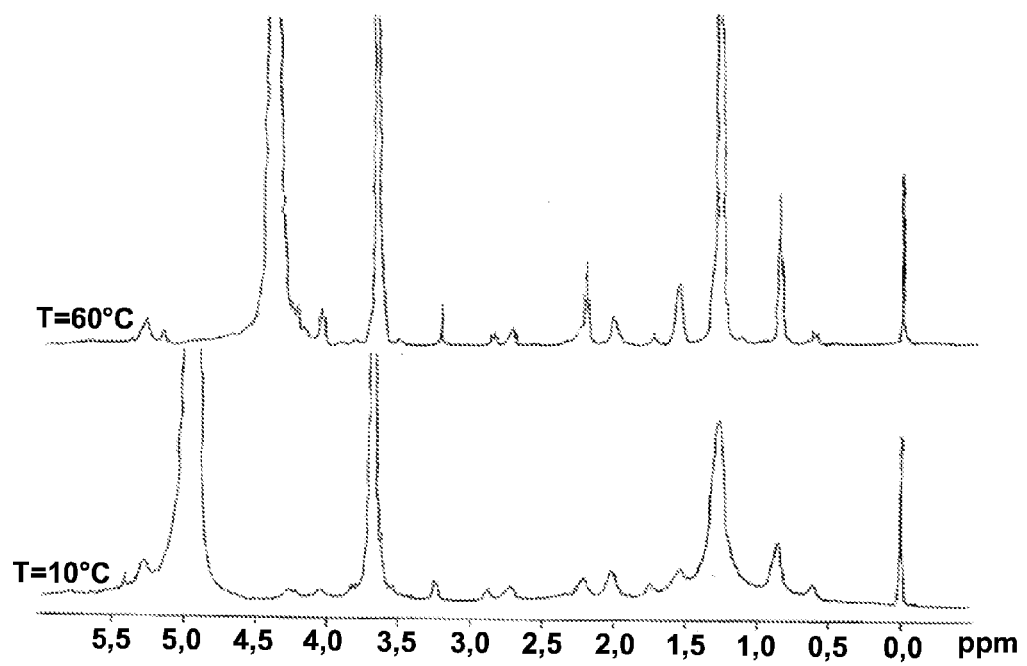
FIG. 10: two $^1$H NMR spectra of the nanoemulsions after production for temperatures of T=10° C. and T=60° C. (Example 6).

Analyses of the nanoemulsion at 10° C. and 60° C. were carried out by proton nuclear magnetic resonance. The peaks associated with the core components of the droplets of the nanoemulsion (oil/solubilising lipid and amphiphilic lipid) (0.9; 1.5; 1.6; 2.0; 2.2; 4.1; 4.2 ppm) observed on the $^1$H NMR spectra are enlarged relative to the reference (4,4-dimethyl-4-silapentane-1-sulfonic acid DSS at 0 ppm), all the more so since the temperature is low, which shows the high internal viscosity of the droplets. The peaks associated with the cosurfactant Myrj53® (3.7 ppm) do not undergo any enlargement, which indicates that the cosurfactant remains at the surface of the droplets, the polyoxyethylene chains being dissolved in the aqueous buffer (FIG. 10).

Example 6b

Demonstration of the Absence of Crystallisation in the Droplets by Differential Scanning Calorimetry A nanoemulsion comprising 150 mg of Suppocire® NC (Gattefossé) (solubilising lipid), 50 mg of soybean oil (Sigma Aldrich) (oil), 228 mg of Myrj53® (ICI Americas Inc.) (cosurfactant), 100 mg of Lipoid® s75 (lecithin, amphiphilic lipid) and a phosphate buffer (PBS) was prepared following the protocol of Example 1.

Figure 11:
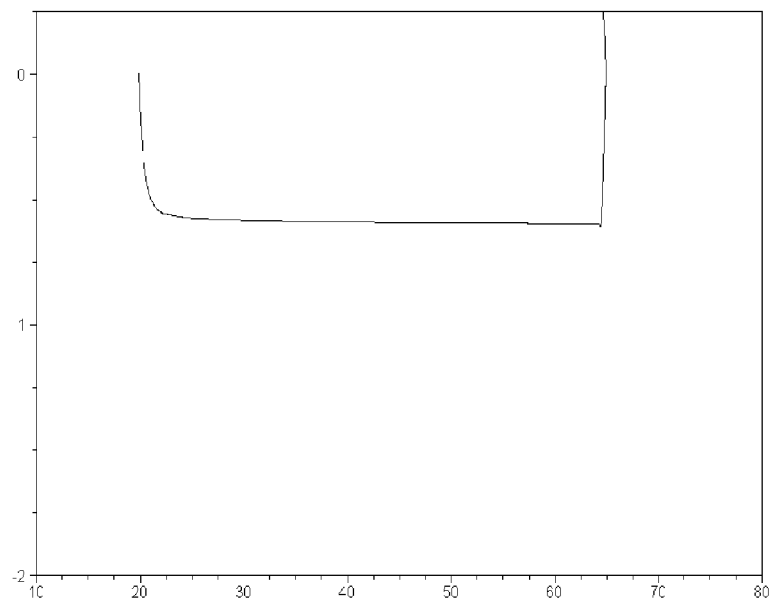
FIGS. 11(A and B): thermograms (heat flux (W/g) as a function of the temperature in ° C.) obtained by differential scanning calorimetry (DSC) of the nanoemulsions after production (a) and after storage for 4 months at ambient temperature (b) using a Universal V3.8B TA device (Example 6).
Figure 11:
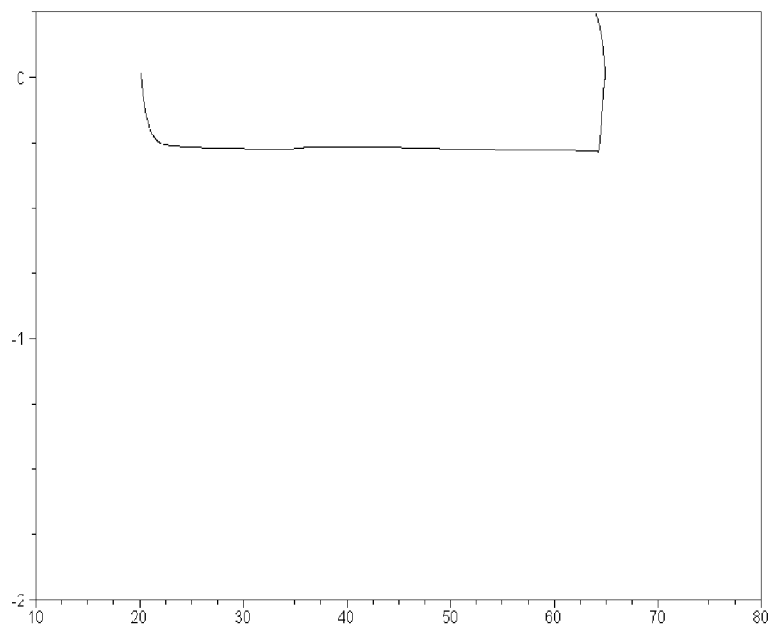

The thermograms obtained by differential scanning calorimetry of the nanoemulsion after preparation and after storage for 4 months at ambient temperature show that no fusion peak is observed either after production or after storage at ambient temperature for 4 months, which indicates that the droplets have not crystallised (FIG. 11).

Example 6c

Demonstration of the Influence of the Composition of the Nanoemulsions on their Physical Stability Three nanoemulsions comprising 228 mg of Myrj53® (ICI Americas Inc.) (cosurfactant), 100 mg of Lipoid® s75 (lecithine, amphiphilic lipid), 1600 µl of phosphate buffer (PBS), Suppocire® NC (Gattefossé) (solubilising lipid) and soybean oil (Sigma Aldrich) (oil) in the amounts specified in Table 3 were prepared following the protocol of Example 1.

TABLE 3

Amounts of Suppocire ® NC and soybean oil in the nanoemulsions.

| Nanoemulsion | NC0 | NC50 | NC100 |
|---|---|---|---|
| Suppocire ® NC | 0 | 100 mg | 200 mg |
| Soybean oil | 200 mg | 100 mg | 0 |

Figure 12:
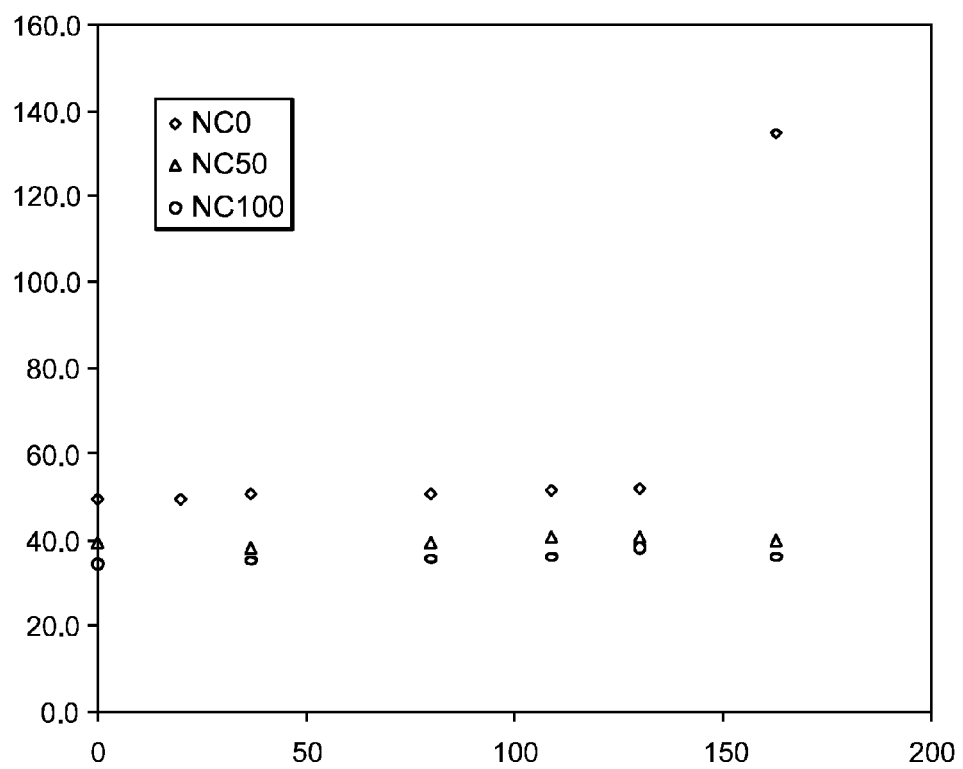
FIG. 12: change in the size of the droplets (in nm) of the nanoemulsion as a function of time (in days) for three nanoemulsions at 40° C. The diamonds represent a nanoemulsion without solubilising lipid and comprising oil, the triangles represent a nanoemulsion comprising a 50/50 mixture of solubilising lipid and oil, and the circles represent a nanoemulsion without oil and comprising solubilising lipid (Example 6).

An accelerated stability test at 40° C. was carried out on the three nanoemulsions obtained. Monitoring of the size/polydispersity of the nanoemulsions over time showed the stabilising effect of the solubilising lipid. While the size of the nanoemulsions without solubilising lipid increases considerably after almost 170 days at 40° C., the nanoemulsions containing solubilising lipid do not exhibit any significant variation in the droplet size (FIG. 12). The results show that the addition of solubilising lipid, to the composition of the nanoemulsions confers better physical stability on the droplets and on the nanoemulsion.

The invention claimed is:

1. A formulation of indocyanine green in the form of a nanoemulsion consisting of:
   indocyanine green,
   at least one phospholipid, and
   at least one solubilising lipid which is solid at 25° C. and which consists of a mixture of saturated fatty acid glycerides comprising:
   at least 10% by weight C12 fatty acids,
   at least 5% by weight C14 fatty acids,
   at least 5% by weight C16 fatty acids, and
   at least 5% by weight C18 fatty acids,
   optionally at least an oil selected from the group consisting of soybean oil, palm oil, arachis oil, olive oil, grapeseed oil, sunflower oil, linseed oil, fish oil and synthetic oils chosen from triglycerides, diglycerides and monoglycerides,
   optionally at least one cosurfactant,
   in which an average size of a dispersed phase is less than 1 micron.

2. The formulation of indocyanine green according to claim 1, comprising at least one oil selected from the group consisting of soybean oil, palm oil, arachis oil, olive oil, grapeseed oil, sunflower oil, fish oil and synthetic oils chosen from triglycerides, diglycerides and monoglycerides.

3. The formulation of indocyanine green according to claim 2, in which the oil has a hydrophilic-lipophilic balance (HLB) of from 3 to 6.

4. The formulation of indocyanine green according to claim 1, comprising at least one oil selected from the group consisting of soybean oil and linseed oil.

5. The formulation of indocyanine green according to claim 1, comprising a cosurfactant.

6. The formulation of indocyanine green according to claim 5, in which the cosurfactant comprises at least one chain composed of ethylene oxide units or of ethylene oxide and propylene oxide units.

7. The formulation of indocyanine green according to claim 6, in which the cosurfactant is selected from the group consisting of polyethylene glycol/phosphatidylethanolamine conjugates (PEG-PE), ethers of fatty acid and polyethylene glycol, esters of fatty acid and polyethylene glycol and block copolymers of ethylene oxide and propylene oxide.

8. The formulation of indocyanine green according to claim 1, in which the at least one solubilising lipid consists of a mixture of saturated fatty acid glycerides comprising:
   from 0% to 20% by weight C8 fatty acids,
   from 0% to 20% by weight C10 fatty acids,
   from 10% to 70% by weight C12 fatty acids,
   from 5% to 30% by weight C14 fatty acids,
   from 5% to 30% by weight C16 fatty acids, and
   from 5% to 30% by weight C18 fatty acids.

* * * * *